(12) United States Patent
Reetz et al.

(10) Patent No.: US 6,824,982 B1
(45) Date of Patent: Nov. 30, 2004

(54) HIGH-THROUGHPUT-SCREENING METHOD FOR DETERMINING ENANTIOSELECTIVITY

(75) Inventors: Manfred T. Reetz, Mülheim an der Ruhr (DE); Michael Heinrich Becker, Ludwigshafen (DE); Detlef Stöckigt, Potsdam (DE); Heinz-Werner Klein, Mülheim an der Ruhr (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/937,512

(22) PCT Filed: Mar. 10, 2000

(86) PCT No.: PCT/EP00/02121

§ 371 (c)(1),
(2), (4) Date: Sep. 25, 2001

(87) PCT Pub. No.: WO00/58504

PCT Pub. Date: Oct. 5, 2000

(30) Foreign Application Priority Data

Mar. 26, 1999 (DE) .......................................... 199 13 858

(51) Int. Cl.$^7$ ................................................. C12Q 1/68
(52) U.S. Cl. ........................................... 435/6; 435/280
(58) Field of Search ................................ 435/4, 6, 280; 562/402

(56) References Cited

U.S. PATENT DOCUMENTS 5,629,424 A * 5/1997 Armstrong et al. .......... 544/316
6,369,223 B2 * 4/2002 Jacobsen et al. ................ 544/4

OTHER PUBLICATIONS

Reetz M. A Method for High Throughput Screening of Enantioselective Catalysts. Angew Chem Int Ed 38(12)1758–61, 1999.*

* cited by examiner

*Primary Examiner*—Ralph Gitomer
(74) *Attorney, Agent, or Firm*—Norris McLaughlin & Marcus (57) ABSTRACT

The present invention relates to a method for determining the enantioselectivity of kinetic resolution processes and of asymmetrically proceeding reactions of prochiral compounds bearing enantiotopic groups by using isotope-labeled substrates so that the reaction products can be quantitatively determined with an isotope-specific detection system, e.g., an ESI mass spectrometer. In connection with automated sample charging, the method can be employed for high throughput screening. The relevant enantioselective conversions can be induced by chiral homogeneous or heterogeneous catalysts, biocatalysts or stoichiometric amounts of optically active agents.

13 Claims, 5 Drawing Sheets

HIGH-THROUGHPUT-SCREENING METHOD FOR DETERMINING ENANTIOSELECTIVITY

This application is a 371 of PCT/EP00/02121 filed on Mar. 10, 2000.

The present invention relates to a method for determining the enantioselectivity of kinetic resolution processes and of asymmetrically proceeding reactions of prochiral compounds bearing enantiotopic groups by using isotope-labeled substrates so that the reaction products can be quantitatively determined with an isotope-specific detection system, e.g., an ESI mass spectrometer. In connection with an automated sampler the method can be employed for high throughput screening. The relevant enantioselective conversions can be induced by chiral homogeneous or heterogeneous catalysts, biocatalysts or stoichiometric amounts of optically active agents.

The development of effective methods for generating extensive libraries of chiral chemical catalysts by methods of combinatorial chemistry [a) G. Liu, J. A. Ellman, J. Org. Chem. 1995, 60, 7712–7713; b) K. Burgess, H.-J. Lim, A. M. Porte, G. A. Sulikowski, Angew. Chem. 1996, 108, 192–194; Angew. Chem., Int. Ed. Engl. 1996, 35, 220–222; c) B. M. Cole, K. D. Shimizu, C. A. Krueger, J. P. A. Harrity, M. L. Snapper, A. H. Hoveyda, Angew. Chem. 1996, 108, 1776–1779; Angew. Chem., Int. Ed. Engl. 1996, 35, 1668–1671; d) C. Gennari, H. P. Nestler, U. Piarulli, B. Salom, Liebigs Ann./Recl. 1997, 637–647] or for the preparation of libraries of enantioselective biocatalysts by in-vitro evolution [M. T. Reetz, A. Zonta, K. Schimossek, K. Liebeton, K.-E. Jaeger, Angew. Chem. 1997, 109, 2961–2963; Angew. Chem., Int. Ed. Engl. 1997, 36, 2830–2932] is currently under investigation. A critical aspect of the success of these novel technologies is the existence of effective and rapid methods for the screening of the enantioselective catalysts or biocatalysts from the respective catalyst libraries. While many effective methods for the screening of large libraries of biologically active compounds are available in the combinatorial chemistry of active substances [a) F. Balkenhohl, C. von dem Bussche-Hünnefeld, A. Lansky, C. Zechel, Angew. Chem. 1996, 108, 2436–2488; Angew. Chem., Int. Ed. Engl. 1996, 35, 2288–2337; b) J. S. Früchtel, G. Jung, Angew. Chem. 1996, 108, 19–46; Angew. Chem., Int. Ed. Engl. 1996, 35, 17–42; c) Chem. Rev. 1997, 97 (2), 347–510 (special edition about combinatorial chemistry); d) S. R. Wilson, A. W. Czarnick, Combinatorial Chemistry: Synthesis and Application, Wiley, N.Y., 1997], the development of methods for the high throughput screening of enantioselective catalysts, biocatalysts or optically active agents is still at the beginning. The determination of the enantiomeric excess (ee) of the products of stereo-selective conversions is normally effected classically by means of gas or liquid chromatography on chiral stationary phases [G. Schomburg, Gaschromatographie: Grundlagen, Praxis, Kapillartechnik, 2nd Ed., VCH, Weinheim, 1987; K. K. Unger, Packings and stationary phases in chromatographic techniques, Series Chromatographic science; Vol. 47, Marcel Dekker, New York, 1990]. Although precise ee values can be determined thereby, such conventional methods have a disadvantage in that only a limited number of samples can be examined per unit time since the times required for analysis depend on the respective retention times.

The first suggestions for solving analytical problems of this kind have been made recently. Thus, for example, in the scope of a study on the in-vitro evolution of enantioselective lipases, a relatively rough test method has been developed according to which the course of enantioselective hydrolyses of chiral carboxylate esters can be determined [M. T. Reetz, A. Zonta, K. Schimossek, K. Liebeton, K.-E. Jaeger, Angew. Chem. 1997, 109, 2961–2963; Angew. Chem., Int. Ed. Engl. 1997, 36, 2830–2932]. Thus, the time course of the hydrolysis of carboxylic acid p-nitrophenol esters of (R)- and (S)-configurations catalyzed by lipase mutants is monitored spectrophotometrically on microtiter plates, whereby the most enantioselective mutants can be identified quickly. Apart from the fact that no exact ee values are possible, this method is limited to the chiral carboxylic acid class of substances. The same applies to a related test method [L. E. Janes, R. J. Kazlauskas, J. Org. Chem. 1997, 62, 4560–4561]. Also subject to this limitation are related methods which are based on the color change of pH indicators during ester hydrolysis [L. E. Janes, A. C. Löwendahl, R. J. Kazlauskas, Chem.—Eur. J. 1998, 4, 2324–2331]. A totally different approach for the identification of chiral catalysts is based on infrared thermography [M. T. Reetz, M. H. Becker, K. M. Kühling, A. Holzwarth, Angew. Chem. 1998, 110, 2792–2795; Angew. Chem., Int. Ed. 1998, 37, 2547–2650]. However, the further development of this method to enable the quantitative analysis of enantioselective reactions still remains to be done.

The present invention remedies these defects by employing partially or completely isotope-labeled substrates or substrates having an isotope distribution which deviates from the natural distribution for kinetic resolution processes or for stereoselective reactions with prochiral substrates containing enantiotopic groups. This permits the use of an isotope-specific detection system, for example, a mass-spectrometric ionization method, for the quantitative determination of the conversion or the relative proportions of the pseudo-enantiomers or of enantiomeric excess.

As compared to previous approaches, the present invention offers the following advantages:

1) Exact determination of the ee values of kinetic resolution processes and of asymmetrically proceeding conversions of prochiral compounds bearing enantiotopic groups, no limitations being made with respect to the class of substances or the type of reaction.
2) Exact determination of the conversion of the reactions mentioned under 1).
3) Rapid or high throughput testing of the data mentioned under 1) and 2), at least 1000 determinations per day being possible in particular.

The detection systems used in the present invention are mass spectrometers, especially those using electro-spray ionization (ESI) [J. B. Fenn, M. Mann, C. K. Meng, S. F. Wong, C. M. Whitehouse, Science (Washington, D.C.) 1989, 246, 64–71] or matrix-assisted laser desorption/ionization (MALDI) [a) K. Tanaka, H. Waki, Y. Ido, S. Akita, Y. Yoshida, T. Yoshida, Rapid Commun. Mass Spectrom. 1988, 2, 151–153; b) M. Karas, F. Hillenkamp, Anal. Chem. 1988, 60, 2299–2301]. In connection with automated sampler (use of one or more sample charging robots and microtiter plates), optionally with the use of several spectrometers, the method according to the invention is suitable as a high throughput screening method.

The method can be used for finding or optimizing chiral catalysts or chiral agents for asymmetrically proceeding reactions. These include:

a) chiral catalysts or chiral agents for the kinetic resolution of alcohols, carboxylic acids, carboxylate esters, amines, amides, olefins, alkynes, phosphines, phosphonites, phosphites, phosphates, halides, oxiranes, thiols, sulfides, sulfones, sulfoxides, sulfonamides, and their derivatives;

b) chiral catalysts (e.g., chiral homogeneous or chirally modified heterogeneous catalysts, chiral metal complexes) or chiral agents for the stereoselective conversion of prochiral compounds whose enantiotopic groups include one or more functional groups from the classes of substances of alcohols, carboxylic acids, carboxylate esters, amines, amides, olefins, alkynes, phosphines, phosphonites, phosphites, phosphates, halides, oxiranes, thiols, sulfides, sulfones, sulfoxides, sulfonamides, or their derivatives;

c) biocatalysts, e.g., enzymes, antibodies, proteins, hormones, phages, ribozymes, peptides or other biopolymers, for the kinetic optical resolution of alcohols, carboxylic acids, carboxylate esters, amines, amides, olefins, alkynes, phosphines, phosphonites, phosphites, phosphates, halides, oxiranes, thiols, sulfides, sulfones, sulfoxides, sulfonamides, and their derivatives, and for the stereoselective conversion of prochiral compounds whose enantiotopic groups include one or more functional groups from the classes of substances of alcohols, carboxylic acids, carboxylate esters, amines, amides, olefins, alkynes, phosphines, phosphonites, phosphites, phosphates, halides, oxiranes, thiols, sulfides, sulfones, sulfoxides, sulfonamides, or their derivatives.

The principle underlying the invention is based on the use of isotope-labeled substrates in the form of pseudo-enantiomers or pseudo-prochiral compounds, as represented in Scheme 1.

If one enantiomeric form in a conventional racemate is isotope-labeled, such compounds are called pseudo-enantiomers. If one enantiotopic group of a prochiral substrate is labeled with isotopes, the compound is called pseudo-prochiral, e.g., pseudo-meso. Depending on what types of enantioselective conversions are to be examined or tested according to the invention, different situations are relevant, such as case a, case b, case c and case d in Scheme 1. In kinetic optical resolution processes of any chiral compounds, 1 and 2, which differ in absolute configuration and in the isotope labeling in the functional groups FG*, are prepared in an optically pure form and mixed in a ratio of 1:1 to simulate a racemate (Scheme 1a). After an enantioselective conversion in which the chemical reaction occurs at the functional group (up to a conversion of 50% in the ideal case of a kinetic optical resolution), true enantiomers 3 and 4 are formed along with unlabeled and labeled achiral by-products 5 and 6, respectively.

The ratios of the intensities of 1/2 and 5/6 in the mass spectra (m/z intensities of the quasi-molecular ions) allow for the quantitative determination of the enantioselectivity (ee values) and of the conversion. Optionally, an internal standard may be used according to the invention. According to circumstances, it may be advantageous to effect the isotope-labeling not in the functional group but in the residue $R^2$ of the substrate as outlined in Scheme 1b. In this case, a new pair of pseudo-enantiomers 3/8 is produced (Scheme 1b), the enantioselectivity and conversion being established according to the invention by measuring the m/z intensities of the quasi-molecular ions of 1/7 and 3/8. Thus, the so-called selectivity factors (s or E values) are automatically accessible in both cases [H. B. Kagan, J. C. Fiaud in Top. Stereochem., Vol. 18 (Eds.: E. L. Eliel, S. H. Wilen), Wiley, N.Y., 1988, p. 249–330].

In the case of prochiral substrates having enantiotopic groups, the synthesis of a single pseudo-prochiral compound is required for the screening system according to the invention. When the relevant substrate is a meso-compound, a corresponding meso-compound 9 is first prepared since the stereo-differentiating reaction to be examined yields a mixture of two MS-detectable pseudo-enantiomers 10 and 11 (Scheme 1c). According to the invention, an analogous procedure applies to other prochiral substrates having enantiotopic groups, such as the use of pseudo-prochiral substrates of type 12 (Scheme 1d).

The FG units in Scheme 1 may be a wide variety of functional groups of organic chemistry. Typical representatives are acyloxy residues (—OC(O)R), thioacyloxy residues (—SC(O)R), amido residues (—NHC(O)R), carboxy residues (—CO$_2$R) in the case of cleavage reactions, such as hydrolyses, and further hydroxy residues (—OH), thiol residues (—SH), amino residues (—NH$_2$ or —NHR), or carboxy residues (—CO$_2$H) in the case of bond-forming reactions, such as acylations or esterifications.

Scheme 1 only serves to illustrate or describe the method according to the invention and does not limit it in any way. Rather, any classes of substances and types of reactions are possible as long as the substrates are either chiral, as naturally in a kinetic optical resolution, or they are prochiral and contain enantiotopic groups.

In order to ensure a high sample throughput, the invention provides a design of equipment as outlined in an illustrative way in Scheme 2. With this combination of commercially available devices or parts of apparatus, it is possible to perform at least 1000 ee determinations per day with an accuracy of ±5%.

EXAMPLE 1

Kinetic Optical Resolution of 1-Phenylethyl Acetate

The hydrolytical kinetic resolution of 1-phenylethyl acetate catalyzed, for example, by enzymes such as lipases (wild type or mutants) is monitored with the configuration described in Scheme 2 within the scope of a high throughput screening, i.e., ee and conversion determinations are performed.

Synthesis of (1S)-1-Phenylethyl Acetate (15):

In a 25 ml nitrogen-purged flask, with exclusion of air and moisture, 8.28 mmol (1.01 g, 1.00 ml) of (S)-1-phenylethanol (Fluka, 99% ee), 12.4 mmol (1.50 equ., 983 mg, 1.00 ml) of pyridine and 15 ml of dichloromethane are charged and cooled down to 0° C. (ice bath). With stirring, 10.8 mmol (1.30 equ., 1.10 g, 1.02 ml) of acetic anhydride is added dropwise over 10 min. Within a period of 12 h, the mixture is warmed up to room temperature and successively extracted twice each with 20 ml of 1 M aqueous hydrochloric acid solution, saturated sodium hydrogencarbonate solution and saturated sodium chloride solution. The organic phase is dried over magnesium sulfate, separated from the desiccant by filtration and freed from solvent in a rotary evaporator. The crude product was purified by chromatography over silica gel (mobile solvent: hexane:ethyl acetate= 9:1). The product fractions are combined and freed from solvent in a rotary evaporator. After drying in an oil-pump vacuum, a clear liquid remains (1.25 g, 7.62 mmol, 92%). Analytics: $^1$H-NMR (CDCl$_3$, 200 MHz): δ=1.52 (d) $^3$J=6.6 Hz [3H], 2.06 (s) [3H], 5.94 (q) $^3$J=6.6 Hz [1H], 7.24–7.38 (m) [5H]; $^{13}$C-{$^1$H}-NMR (CDCl$_3$, 50 MHz): δ=21.4 (s), 22.2 (s), 72.3 (s), 126.1 (s), 127.9 (s), 128.5 (s), 141.7 (s), 170.3 (s); MS (EI, 70 eV, pos. ions): m/z (% rel. int.): 164 (25) [M$^+$], 122 (77), 107 (36), 105 (69), 104 (100), 103 (24), 79 (27), 78 (27), 77 (43), 51 (24), 43 (90); EA: C: 72.95%

(calc. 73.15%), H: 7.28% (calc. 7.37%); GC (Hewlett Packard 5890, 25 m fused silica, 0.25 inner diameter, 2,6-dimethyl-3-pentyl-β-CD (95% methyl-/5% phenylpolysiloxane), FID, 80° C., 4° C. min$^{-1}$, 120° C. 0.2 min iso, 0.63 bar hydrogen): 99.8% ee.

Synthesis of (1R)-1-Phenylethyl Trideuteroacetate (16):

In a 25 ml nitrogen-purged flask, with exclusion of air and moisture, 8.28 mmol (1.01 g, 1.00 ml) of (R)-1-phenylethanol (Fluka, 99% ee), 12.4 mmol (1.50 equ., 983 mg, 1.00 ml) of pyridine and 15 ml of dichloromethane are charged and cooled down to 0° C. (ice bath). With stirring, 10.8 mmol (1.3 equ., 1.16 g, 1.02 ml) of d$_6$-acetanhydride (99 atomic percent of D, Aldrich) is added dropwise over 10 min. Within a period of 12 h, the mixture is warmed up to room temperature and successively extracted twice each with 20 ml of 1 M aqueous hydrochloric acid solution, saturated sodium hydrogencarbonate solution and saturated sodium chloride solution. The organic phase is dried over magnesium sulfate, separated from the desiccant by filtration and freed from solvent in a rotary evaporator. The crude product was purified by chromatography over silica gel (mobile solvent: hexane:ethyl acetate=9:1). The product fractions are combined and freed from solvent in a rotary evaporator. After drying in an oil-pump vacuum, a clear liquid remains (1.28 g, 7.65 mmol, 92%). Analytics: $^1$H-NMR (CDCl$_3$, 200 MHz): δ=1.53 (d) $^3$J=6.6 Hz [3H], 5.88 (q) $^3$J=6.6 Hz [1H], 7.24–7.36 (m) [5H]; $^{13}$C-{$^1$H}-NMR (CDCl$_3$, 50 MHz): δ=22.2 (s), 72.3 (s), 126.1 (s), 127.7 (s), 128.5 (s), 141.7 (s), 170.3 (s); MS (EI, 70 eV, pos. ions): m/z (% rel. int.): 167 (24) [M$^+$], 123 (77), 108 (39), 105 (67), 104 (100), 103 (25), 78 (27), 77 (35), 51 (19), 46 (65), 43 (14); EA: C: 71.77% (calc. 71.83%), H+D: 6.98% (calc. 7.23%); GC (Hewlett Packard 5890, 25 m fused silica, 0.25 inner diameter, 2,6-dimethyl-3-pentyl-β-CD (95% methyl-/5% phenylpolysiloxane), FID, 80° C., 4° C. min$^{-1}$, 120° C. 0.2 min iso, 0.63 bar hydrogen): 99.8% ee.

Figure 1:
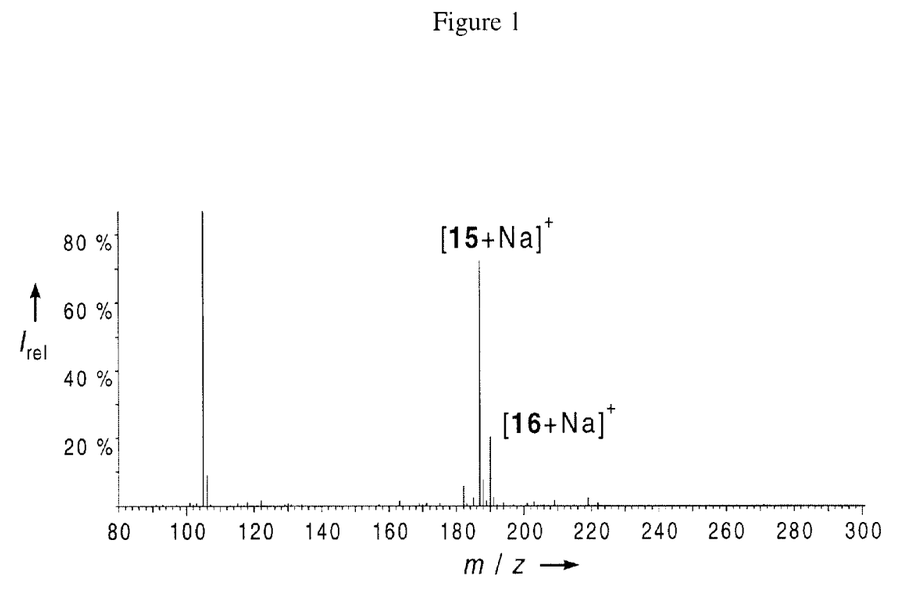

In preliminary experiments, the pseudo-enantiomers 15 and 16 were mixed at different ratios. The resulting mixtures were first examined by conventional gas chromatography on a chiral stationary phase to establish the pseudo-ee values. The same samples were then examined by ESI-MS. A typical ESI mass spectrum is shown in FIG. 1. A comparison between the two sets of data shows correspondence within ±5% (Table 1).

TABLE 1

| Sample | ee (GC) | ee (ESI-MS) |
|---|---|---|
| 1 | 100 | 100 |
| 2 | 91 | 90 |
| 3 | 81 | 79 |
| 4 | 74 | 73 |
| 5 | 60 | 57 |
| 6 | 56 | 54 |
| 7 | 48 | 48 |
| 8 | 28 | 27 |
| 9 | 10 | 10 |
| 10 | 23 | 20 |
| 11 | 40 | 38 |
| 12 | 45 | 43 |
| 13 | 55 | 53 |
| 14 | 65 | 60 |
| 15 | 75 | 74 |
| 16 | 95 | 93 |
| 17 | 100 | 100 |

Subsequently, 1:1 mixtures of the pseudo-enantiomers 15/16 were hydrolyzed with different lipases (wild type and mutants, e.g., from *P. aeruginosa*) on micro-titer plates examined for enantioselectivity and conversion with the screening system described in Scheme 2. About 1000 exact ee determinations could be performed per say. In detail, 0 μl of a 1 mM 1:1 mixture of 15 and 16 in CH$_3$OH was infected into the Rheodyne® valve of an ESI-MS system (ESI-MS conditions: HP 5989B MS pole Engine Quadrupole Mass Spectrometer, equipped with an HP 59987B API electrospray source II with hexapole ion guidance (Analytica of Branford) and ChemStation®; data recording: scan spectra in a positive ion mode; m/z 90–300; in 0.1 m/z steps, unit resolution, Gaussian mass filter m/z 0.3 min; Gaussian time filter 0.05 min; API source conditions: potential difference between the spray needle and the first electrode: –5250 V, pressure of the N$_2$ nebulizer gas: 80 psi, flow rate of the N$_2$ drying gas about 9 l min$^{-1}$ (150° C.), solvent flow 0.06 ml min$^{31\ 1}$, CH$_3$OH:H$_2$O=8:2). About 20–30 ESI mass spectra were summed up, and the proportions of 15 and 16 were determined by the absolute intensities of the signals of the corresponding sodium adducts ([15+Na]$^+$ and [16+Na]$^+$, FIG. 1). The ratios of the signals (and thus the ee values of the synthetic mixtures of 15 and 16) were automatically transferred from the m/z intensity list of the individual measurements into an Excel® table using a macro instruction.

EXAMPLE 2

Kinetic Optical Resolution of 2-Phenylpropionic Acid

In this Example, the enantioselective esterification of 2-phenylpropionic acid within the scope of a lipase-catalyzed kinetic optical resolution is described. Thus, the pseudo-enantiomers 21/22 were first synthesized.

Synthesis of 22:
Synthesis of (4R)-Benzyl-3-N-benzyloxy-2-oxazolidine-2-one:

In a 250 ml nitrogen-purged flask, with exclusion of air and moisture, 24.0 mmol (4.52 g) of (4R)-benzyloxazolidine-2-one (Fluka) is dissolved in 80 ml of tetrahydrofuran and cooled down to –78° C. (dry ice bath). With stirring, 24.0 mmol (15.0 ml of a 1.6 M solution) of n-butyllithium in hexane is added dropwise over 15 min. After 90 min, a solution of freshly distilled phenylacetic chloride (24.0 mmol, 3.71 g, 3.18 ml) and 10 ml of tetrahydrofuran is added dropwise over 10 min at –78° C. After completion of the dropwise addition, the dry ice bath is replaced by an ice bath. After stirring at 0° C. for 1 h, the reaction is stopped by the addition of 25 ml of a saturated ammonium chloride solution, followed by stirring at 0° C. for another hour. The reaction mixture is subsequently transferred to a 250 ml flask, and the organic solvent is removed in a rotary evaporator. The residue is extracted three times with 60 ml of diethyl ether, twice with 70 ml each of 1 M aqueous sodium hydroxide solution, 1 M aqueous hydrochloric acid solution and saturated sodium chloride solution. The combined organic phases are dried over magnesium sulfate, separated from the desiccant by filtration and freed from solvent in a rotary evaporator. The crude product was purified by chromatography over silica gel (mobile solvent: hexane:ethyl acetate=3:1). The product fractions are combined and freed from solvent in a rotary evaporator. After drying in an oil-pump vacuum, a clear liquid remains (5.88 g, 19.9 mmol, 83%). Analytics: $^1$H-NMR (CDCl$_3$, 300 MHz): δ=2.67 (dd), $^3$J=9.5 Hz, $^3$J=13.4 Hz [1H], 3.27 (dd) $^3$J=3.3 Hz, $^2$J=13.4 Hz [1H], 4.14–4.23 (m) [1H], 4.26 (d) $^2$J=15.7 Hz [1H], 4.35 (d) $^2$J=15.7 Hz [1H], 4.65–4.70 (m) [1H], 7.25–7.36 (m) [10H]; $^{13}$C-{$^1$H}-NMR (CDCl$_3$, 75 MHz): δ=37.7 (s), 41.6 (s), 55.3 (s), 66.1 (s), 127.26 (s), 127.34 (s), 128.3 (s), 128.6 (s), 128.9 (s), 129.4 (s), 129.8 (s), 130.0 (s), 133.5 (s), 135.1 (s), 153.4 (s), 171.2 (s); MS (EI, 70 eV, pos. ions): m/z (% rel. int.): 295 (44) [M$^+$], 178 (6), 119 (16), 118 (100), 117 (9), 91 (88), 90 (11), 65 (12); EA: C: 73.31% (calc. 73.20%), H: 5.72% (calc. 5.80%), N: 4.68% (calc. 4.74%).

Synthesis of (4R)-Benzyl-3-N-((2R)-3,3,3-trideutero-2-phenylpropionyl)oxazoli-dine-2-one:

In a 250 ml nitrogen-purged flask, with exclusion of air and moisture, 18.0 mmol (3.29 g) of sodium hexamethyidisilazide is dissolved in about 50 ml of tetrahydro-furan and cooled down to −78° C. (dry ice bath). With stirring, a solution of 18.0 mmol (5.30 g) of (4R)-benzyl-3-N-benzyloxy-2-oxazolidine-2-one in 25 ml of tetrahydrofuran is added dropwise over 30 min. After 90 min of stirring at −78° C., a solution of 90.0 mmol (13.0 g, 5.60 ml) of d$_3$-methyl iodide (99 atomic percent of D, Aldrich) and 20 ml of tetrahydrofuran is added dropwise over 30 min. Stirring is continued at −78° C. for another 12 h, and then the reaction is stopped by the addition of 30 ml of a saturated ammonium chloride solution. After warming up to room temperature, the reaction mixture is transferred to a 250 ml flask, and the organic solvent is removed in a rotary evaporator. The residue is extracted three times with 60 ml of diethyl ether. The combined ethereal phases are extracted twice with 50 ml each of 10% aqueous hydrochloric acid solution, saturated sodium hydrogencarbonate solution and saturated sodium chloride solution. The combined organic phases are dried over magnesium sulfate, separated from the desiccant by filtration and freed from solvent in a rotary evaporator. The crude product is recrystallized from ether/ethyl acetate. After filtration and drying in an oil-pump vacuum, a colorless solid is obtained (4.67 g, 14.9 mmol, 83%). Analytics: $^1$H-NMR (CDCl$_3$, 300 MHz): δ=2.80 (dd) $^3$J=9.8 Hz, $^2$J=13.3 Hz [1H], 3.35 (dd) $^3$J=3.2 Hz, $^2$J=13.3 Hz [1H], 4.02–4.13 (m) [2H], 4.55–4.62 (m) [2H], 5.10 (s) [1H], 7.21–7.38 (m) [10H]; $^{13}$C-{$^1$H}-NMR (CDCl$_3$, 75 MHz): δ=37.9 (s), 42.9 (s), 55.8 (s), 65.9 (s), 127.3 (s), 127.4 (s), 128.1 (s), 128.7 (s), 129.0 (s), 129.4 (s), 135.3 (s), 140.2 (s), 152.9 (s), 174.6; MS (EI, 70 eV, pos. ions): m/z (% rel. int.): 312 (34) [M$^+$], 135 (100), 108 (72), 107 (18), 91 (14); EA: C: 73.16% (calc. 73.05%), H+D: 6.00% (calc. 6.13%), N: 4.41% (calc. 4.48%).

Synthesis of (2R)-3,3,3-Trideutero-2-phenylpropionic Acid (22):

In a 250 ml nitrogen-purged flask, 11.6 mmol (3.64 g) of (4R)-benzyl-3-N-((2R)-3,3,3-trideutero-2-phenylpropionyl)oxazolidine-2-one is dissolved in about 100 ml of tetrahydrofuran, and the solution obtained is cooled down to 0° C. A solution of 23.3 mmol (978 mg) of lithium hydroxide monohydrate in 18.0 ml of 30% aqueous hydrogen peroxide solution is added with stirring. This is followed by stirring for 18 h at 0° C. The reaction is stopped at 0° C. by the dropwise addition of 20 ml of a saturated sodium sulfite solution, the reaction mixture is transferred to a 250 ml flask, and the organic solvent is removed in a rotary evaporator. The residue is extracted three times with 70 ml each of dichloromethane. The aqueous phase is acidified to pH 5 with 10% hydrochloric acid, followed by extracting three times with 70 ml each of diethyl ether. The combined ethereal phases are dried over magnesium sulfate, separated from the desiccant by filtration, and the solvent is removed in a rotary evaporator. After drying in an oil-pump vacuum, a colorless liquid remains (8.60 mmol, 1.32 g, 74%). Analytics: $^1$H-NMR (CDCl$_3$, 300 MHz): δ=3.72 (s) [1H], 7.24–7.35 (m) [5H], 11.5 (s) [1H]; $^{13}$C-{$^1$H}-NMR (CDCl$_3$, 75 MHz): δ=45.2 (s), 127.4 (s), 127.6 (s), 128.7 (s), 139.7 (s), 180.8 (s); MS (EI, 70 eV, pos. ions): m/z (% rel. int.): 153 (24) [M$^+$], 108 (100), 91 (8), 82 (5), 81 (8), 80 (5), 79 (10), 78 (8), 77 (6), 43 (11); EA: C: 70.35% (calc. 73.56%), H+D: 6.62% (calc. 6.58%); HPLC (Varian 5560, stat. phase: 250 mm Chiracel OD-H, 4.6 mm i.d., mob. phase: n-heptane:2-propanol:tri-fluoroacetic acid=98:2:0.1, 298 K, 1.2 MPa, 0.5 ml min$^{-1}$, detection: UV 254 nm): 99.4% ee.

Figure 2:
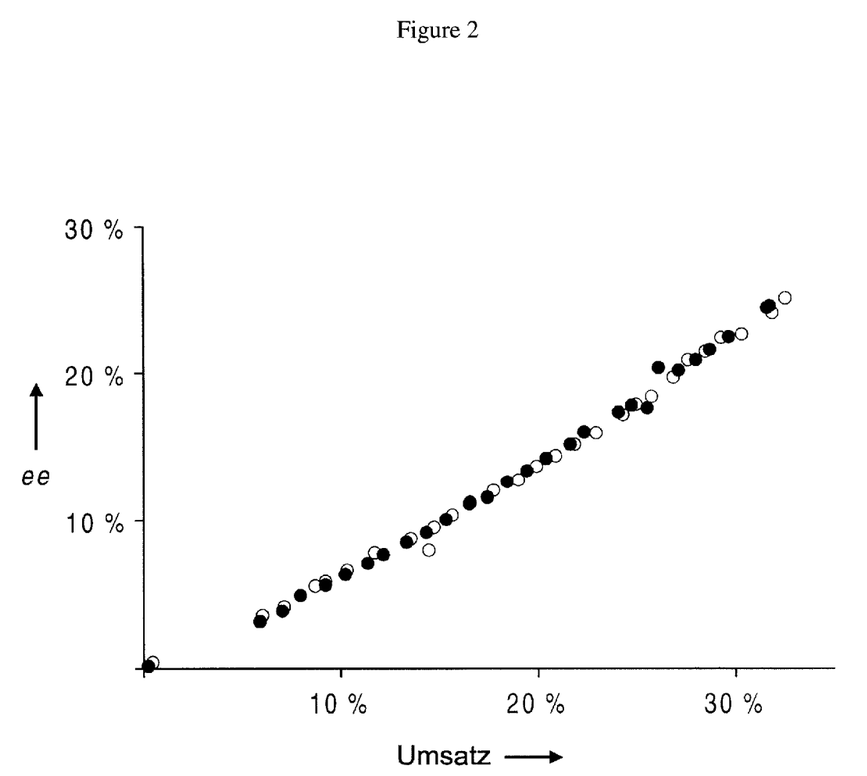

To exclude any interfering secondary isotope effects, the reaction of the pseudo-enantiomers 21/22 was compared with the reaction of the true racemate of 21 in a preliminary experiment. The data in FIG. 2 do not show any essential differences in the result so that secondary kinetic isotope effects which could distort the results from the conversions can be excluded.

Then, about 1000 ee and conversion determinations were performed per day using the configuration in Scheme 2 using lipases (wild type and mutants).

EXAMPLE 3

Enantioselective Hydrolysis of Meso-1,4-Diacetoxy-2-Cyclopentene

This example relates to the reactions of a prochiral compound bearing enantiotopic groups (acetoxy groups in this case)

Synthesis of (1S,4R)-cis-1-Acetoxy-4-trideuteroacetoxy-2-cyclopentene (25):

In a 100 ml nitrogen-purged flask, with exclusion of air and moisture, 5.79 mmol (823 mg) of (1S,4R)-cis-4-acetoxy-2-cyclopentene-1-ol (Fluka, 99% ee), 6.95 mmol (1.20 equ., 550 mg, 0.560 ml) of pyridine and 50 ml of dichloromethane are charged and cooled down to 0° C. (ice bath). With stirring, 6.36 mmol (1.10 equ., 688 mg, 600 µl) of d$_6$-acetanhydride (99 atomic percent of D, Aldrich) is added dropwise over 10 min. Within a period of 12 h, the mixture is warmed up to room temperature and successively extracted twice each with 40 ml of 1 M aqueous hydrochloric acid solution, saturated sodium hydrogencarbonate solution and saturated sodium chloride solution. The organic phase is dried over magnesium sulfate, separated from the desiccant by filtration and freed from solvent in a rotary evaporator. The crude product was purified by chromatography over silica gel (mobile solvent: hexane:ethyl acetate= 3:1). The product fractions are combined and freed from solvent in a rotary evaporator. After drying in an oil-pump vacuum, a clear liquid remains (1.01 g, 5.40 mmol, 93%). Analytics: $^1$H-NMR (CDCl$_3$, 300 MHz): δ=1.71–1.78 (m) [2H], 2.07 (s) [3H], 2.83–2.93 (m) [2H], 5.55 (dd) $^3$J=3.8 Hz, 23=7.5 Hz [2H], 6.10 (s) [2H]; $^{13}$C-{$^1$H}-NMR (CDCl$_3$, 75 MHz): δ=21.5 (s), 37.5 (s), 76.9 (s), 135.0 (s), 171.1 (s); MS (EI, 70 eV, pos. ions): m/z (% rel. int.): 128 (9), 127 (3), 125 (9), 124 (3), 84 (17), 83 (81), 82 (82), 81 (16), 55 (6), 54 (24), 46 (100), 43 (92); EA: C: 57.75% (calc. 57.74%), H+D: 6.52% (calc. 6.46%).

Then, in preliminary experiments, the hydrolysis of the substrate 25 with an inactive lipase mutant (*P. aeruginosa* mutant) and an active enzyme (pig liver esterase, Sigma) was examined. Representative mass spectra are shown in FIGS. 3a and 3b.

Figure 3A:
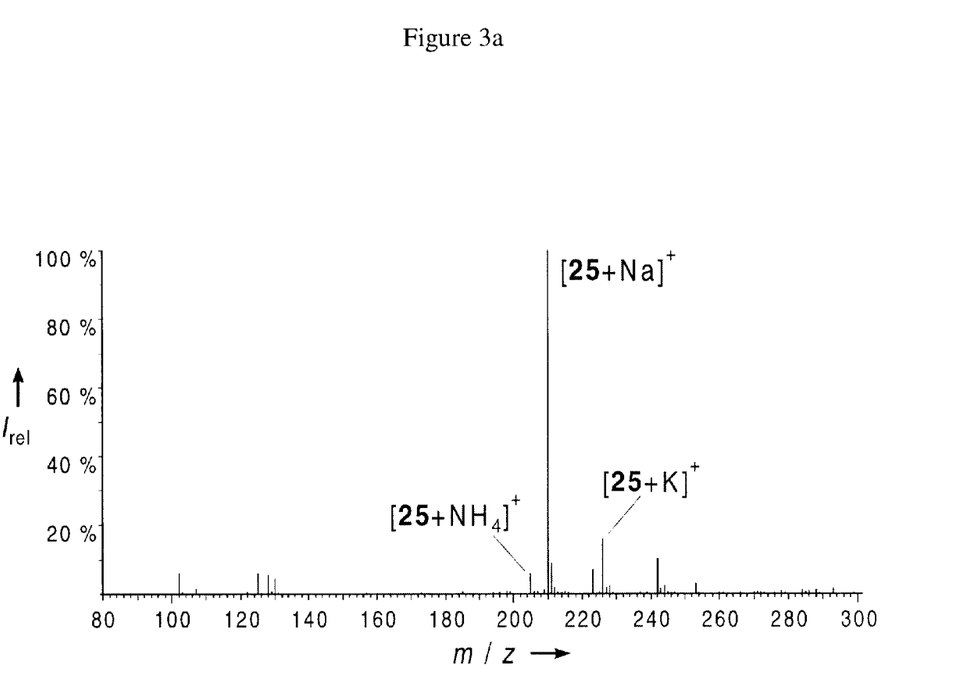
Figure 3B:
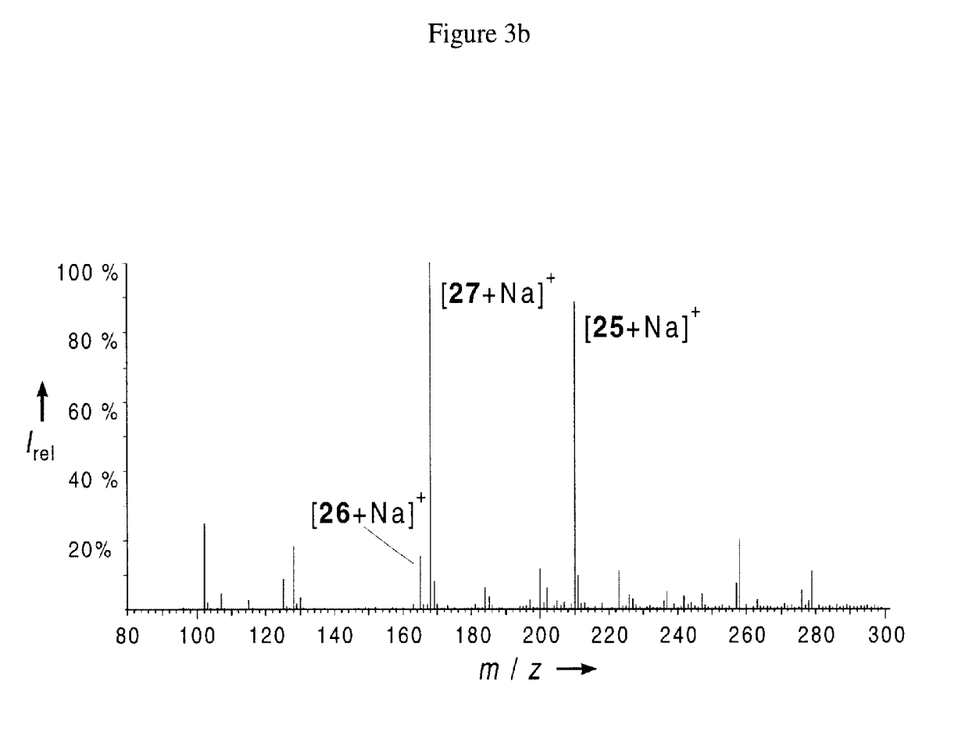

The data in FIG. 3a confirm the absence of reaction while the data in FIG. 3b lead to an ee value of 73%. The independent analysis by conventional gas chromatography yielded an ee value of 73%, in excellent correspondence with the ESI-MS analysis. Then, 1100 samples per day were analyzed for ee values.

EXAMPLE 4

Enantioselective Hydrolysis of Bisnaphthyl Acetates

In this Example, the enantioselective hydrolysis of a 1:1 mixture of the pseudoe-nantiomers 28 and 29 was examined.

Thus, the pseudo-enantiomers 28 and 29 were prepared in an optically pure form.

Synthesis of (S,S)-1,1'-Bisnaphthyl-2,2'-diacetate (28):

In a 50 ml nitrogen-purged flask, with exclusion of air and moisture, 5.00 mmol (1.43 g) of (S,S)-1,1'-bis-2-naphthol (>99.9% ee) was dissolved in 20 ml of dichloromethane, mixed with 15.0 mmol (3.00 equ., 1.19 g, 1.21 ml) of pyridine and cooled down to 0° C. (ice bath). With stirring, 12.5 mmol (2.50 equ., 985 mg, 888 µl) of acetyl chloride is added dropwise over 5 min. Within a period of 12 h, the mixture is warmed up to room temperature and successively extracted twice each with 20 ml of 1 M aqueous hydrochloric acid solution, saturated sodium hydrogencarbonate solution and saturated sodium chloride solution. The organic phase is dried over magnesium sulfate, separated from the desiccant by filtration and freed from solvent in a rotary evaporator. The crude product was purified by chromatography over silica gel (mobile solvent: hexane:ethyl acetate= 7:3). The product fractions are combined and freed from solvent in a rotary evaporator. After drying in an oil-pump vacuum, a colorless solid remains (1.88 g, 4.99 mmol, 99%). Analytics: $^1$H-NMR (d$_6$-DMSO, 300 MHz): δ=1.83 (s) [2H], 6.94 (d) J=8.3 Hz [2H], 7.29–7.34 (m) [2H], 7.48–7.55 (m) [4H], 8.05–8.15 (m) [4H]; $^{13}$C-{$^1$H}-NMR (d$_6$-DMSO, 75 MHz): δ=20.4 (s), 122.4 (s), 122.6 (s), 125.4 (s), 125.7 (s), 126.8 (s), 128.2 (s), 129.5 (s), 131.0 (s), 132.7 (s), 146.6 (s), 168.8 (s); MS (EI, 70 eV, pos. ions): m/z (% rel. int.): 370 (13) [M$^+$], 328 (37), 286 (100), 268 (9), 257 (7), 239 (10), 46 (11); IR (KBr): ṽ (cm$^{-1}$)=3055 (w), 3019 (w), 2936 (w), 1760 (s), 1622 (m), 1595 (m), 1508 (m), 1472 (m), 1430 (m), 1367 (s), 1215 (s), 1130 (s), 1074 (m), 1012 (m), 813 (m), 761 (m); EA: C: 77.53% (calc. 77.82%), H: 4.92% (calc. 4.90%).

Synthesis of (R,R)-1,1'-Bisnaphthyl-2,2'-bis (trideuteroacetate) (29):

In a 50 ml nitrogen-purged flask, with exclusion of air and moisture, 5.00 mmol (1.43 g) of (R,R)-1,1'-bis-2-naphthol (>99.9% ee) was dissolved in 20 ml of dichloromethane, mixed with 15.0 mmol (3.00 equ., 1.19 g, 1.21 ml) of pyridine and cooled down to 0° C. (ice bath). With stirring, 12.5 mmol (2.50 equ., 1.019 g, 889 µl) of d$_3$-acetyl chloride (>99 atomic percent of D, Aldrich) is added dropwise over 5 min. Within a period of 12 h, the mixture is warmed up to room temperature and successively extracted twice each with 20 ml of 1 M aqueous hydrochloric acid solution, saturated sodium hydrogencarbonate solution and saturated sodium chloride solution. The organic phase is dried over magnesium sulfate, separated from the desiccant by filtration and freed from solvent in a rotary evaporator. The crude product was purified by chromatography over silica gel (mobile solvent: hexane:ethyl acetate=7:3). The product fractions are combined and freed from solvent in a rotary evaporator. After drying in an oil-pump vacuum, a colorless solid remains (1.85 g, 4.99 mmol, 99%). Analytics: $^1$H-NMR (d$_6$-DMSO, 300 MHz): δ=6.94 (d) J=8.3 Hz, 7.27–7.34 (m) [2H], 7.48–7.55 (m) [4H], 8.05–8.15 (m) [4H]; $^{13}$C-{$^1$H}-NMR (d$_6$-DMSO, 75 MHz): δ=20.4 (s), 122.4 (s), 122.6 (s), 125.4 (s), 125.7 (s), 126.8 (s), 128.2 (s), 129.5 (s), 131.0 (s), 132.7 (s), 146.6 (s), 168.8 (s); MS (EI, 70 eV, pos. ions): m/z (% rel. int.): 376 (17) [M$^+$], 332 (41), 288 (100), 268 (6), 259 (5), 240 (5), 46 (11); IR (KBr):ṽ (cm$^{-1}$)=(w), 3019 (w). 2268 (w), 2147 (w), 2092 (w), 1755 (s), 1622 (m), 1595 (m), 1509 (m), 1471 (m), 1231 (s), 1146 (s), 1075 (s), 1059 (s), 819 (s), 804 (s), 755 (s); EA: C: 76.23% (calc. 76.85%), H+D: 4.89% (calc. 4.82%).

Within the scope of a high throughput screening for ee and conversion determinations, the design of equipment as described in Scheme 3 was used.

Again, 1:1 mixtures of the pseudo-enantiomers were prepared and employed in the high throughput screening of lipase-catalyzed kinetic optical resolution processes.

Thus, a reflex II MALDI-TOF MS (matrix-assisted laser desorption/ionization time-of-flight mass spectrometer) of Bruker-Franzen Analytik GmbH of Bremen, Germany, was used. The device is equipped with an N$_2$ laser (264 nm) and a 1 GHz Digitizer. A maximum of 40 spectra was automatically recorded and summed up.

Each sample was mixed 1:1 (v/v) with a matrix solution (5% trihydroxyacetophenone solution in CH$_3$OH) using a sample preparation robot and pipetted onto the MALDI target.

Figure 4:
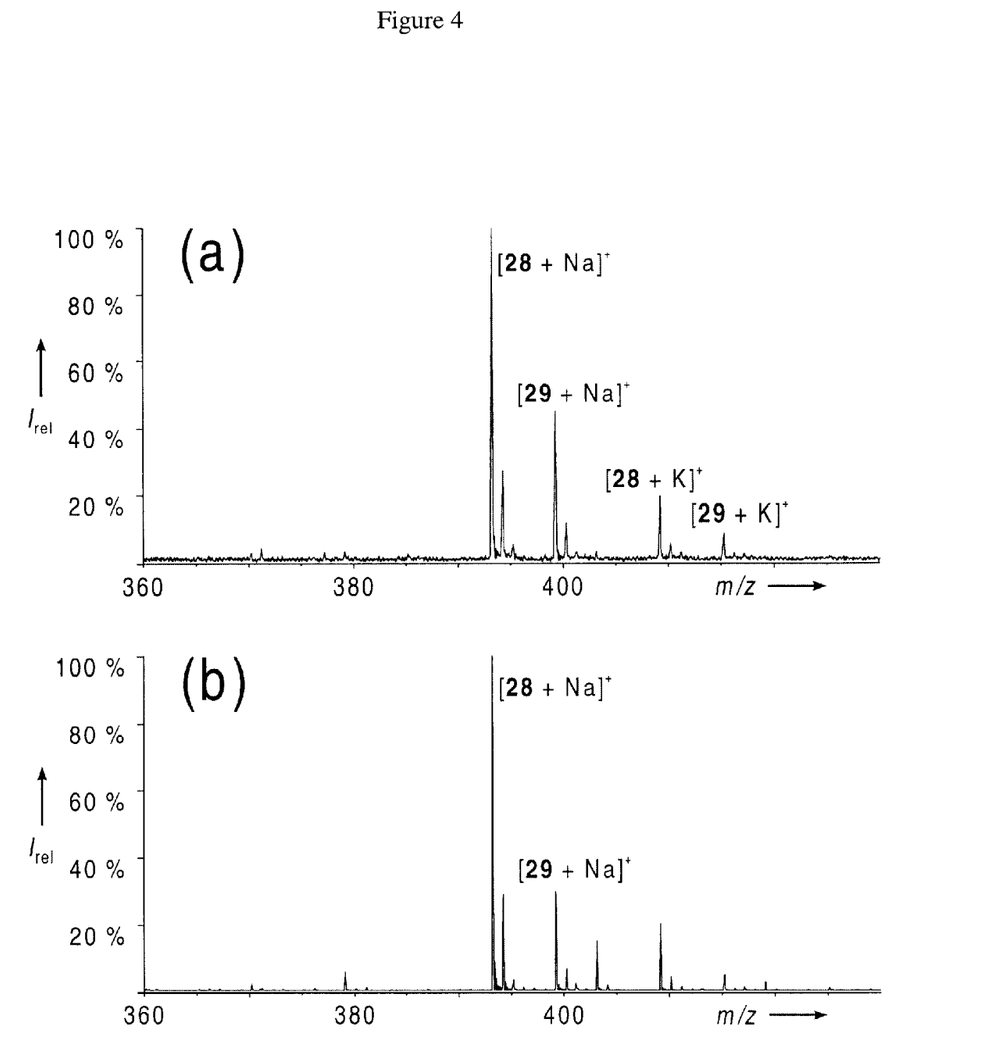

In FIG. 4, segments of selected MALDI mass spectra of reactions of the pseudo-enantiomers 28 and 29 with pig liver esterase (Sigma) are shown. From the signal intensities of [28+Na]$^+$ and [29+Na]$^+$, the enantiomeric excesses were determined (FIG. 4a: 40% ee, FIG. 4b: 54% ee).

What is claimed is:

1. A method for determining the enantioselectivity of a process selected from the group consisting of i) kinetic resolutions of chiral substrates and ii) stereoselective reactions with prochiral substrates comprising enantiotopic groups, said method comprising:

a) providing at least one chiral substrate or at least one prochiral substrate containing an enantiotopic group, said at least one chiral substrate or at least one prochiral substrate containing an enantiotopic group having an isotope distribution which differs from the natural distribution, or being partially or completely isotope-labeled;

b) conducting said process; and c) quantitatively determining any conversion or the relative proportions of any pseudo-enantiomers or any enantiomeric excess using a mass-spectrometric ionization method to give an indication of the enantioselectivity of the process.

2. The method according to claim 1, wherein said quantitatively determining is performed for a series of samples using a sample charging robot.

3. The method according to claim 2, wherein the samples are transferred by one or more sample charging robots from one or more microtiter plates to one or more mass spectrometers.

4. The method according to claim 1, wherein APCI (atmospheric pressure chemical ionization), CI (chemical ionization), EI (electron ionization), ESI (electrospray ionization), FAB (fast atom bombardment), FD (field desorption), LILBID (laser induced liquid beam ionization desorption), LSIMS (liquid secondary ion mass spectrometry), MALDI (matrix-assisted laser desorption/ionization), PB (particle beam), PD (plasma desorption), SIMS (secondary ion mass spectrometry) or TSP (thermospray) or a combination of such ionization methods is used as the mass-spectrometric ionization method.

5. The method according to claim 1, which is conducted for finding or optimizing catalysts which catalyze reactions asymmetrically.

6. The method according to claim 5, which is conducted for finding catalysts for the kinetic resolution of alcohols, carboxylic acids, carboxylate esters, amines, amides, olefins, alkynes, phosphine, phosphonites, phosphites, phosphates, halides, oxiranes, thiols, sulfides, sulfones, sulfoxides, sulfonamide, and their derivatives.

7. The method according to claim 5, which is conducted for finding chiral catalysts or agents for the stereoselective conversion of prochiral compounds whose enantiotopic groups include one or more functional groups from the classes of substances of alcohols, carboxylic acids, carboxylate esters, amines, amides, olefin, alkynes, phosphine, phosphonites, phosphites, phosphates, halides, oxiranes, thiols, sulfides, sulfones, sulfoxides, sulfonamide, or their derivatives.

8. The method according to claim 5, which is conducted for finding biocatalysts for stereoselective synthesis.

9. The method according to claim 8, wherein said biocatalysts are enzymes, antibodies, proteins, hormones, phages, ribozymes, peptides or other biopolymers.

10. The method according to claim 5, which is conducted for finding chiral homogeneous catalysts for stereoselective synthesis.

11. The method according to claim 5, which is conducted for finding chiral metal complexes for stereoselective synthesis.

12. The method according to claim 5, which is conducted for finding chirally modified heterogeneous catalysts for stereoselective synthesis.

13. The method according to claim 1, which is conducted for finding chiral agents which result in the enrichment of one enantiomer in reactions.

* * * * *